US00RE44512E

(19) United States
(12) Reissued Patent
Glover et al.

(10) Patent Number: US RE44,512 E
(45) Date of Reissued Patent: Oct. 1, 2013

(54) METHODS FOR PRODUCING RECOMBINANT PROTEINS

(75) Inventors: David John Glover, Slough (GB); Mukesh Sehdev, Slough (GB); Dominic Gambier Reeks, High Wycombe (GB)

(73) Assignee: UCB Pharma S.A. (BE)

(21) Appl. No.: 13/547,892

(22) Filed: Jul. 12, 2012

Related U.S. Patent Documents

Reissue of:
(64) Patent No.: 7,754,447
Issued: Jul. 13, 2010
Appl. No.: 10/571,367
PCT Filed: Sep. 2, 2004
PCT No.: PCT/GB2004/003747
§ 371 (c)(1),
(2), (4) Date: Jun. 20, 2006
PCT Pub. No.: WO2005/024000
PCT Pub. Date: Mar. 17, 2005

(30) Foreign Application Priority Data

Sep. 9, 2003 (GB) ..... 0321100.0

(51) Int. Cl.
*C12P 21/04* (2006.01)
*C12N 5/00* (2006.01)
*C12Q 1/68* (2006.01)

(52) U.S. Cl.
USPC ..... 435/6.14; 435/69.1; 435/29; 435/71.1

(58) Field of Classification Search
None
See application file for complete search history.

(56) References Cited

U.S. PATENT DOCUMENTS

| | | | | |
|---|---|---|---|---|
| 5,585,089 | A | 12/1996 | Queen et al. | 424/133.1 |
| 5,665,866 | A | 9/1997 | Weir et al. | 530/390.5 |
| 6,716,602 | B2 * | 4/2004 | Andersen et al. | 435/69.1 |

FOREIGN PATENT DOCUMENTS

| | | | |
|---|---|---|---|
| EP | 0 335 567 | A2 | 10/1989 |
| WO | WO 91/09967 | A1 | 7/1991 |
| WO | WO 92/02551 | A1 | 2/1992 |
| WO | 0240697 | | 5/2002 |
| WO | 2005017162 | | 2/2005 |

OTHER PUBLICATIONS

Shokri et al., "Growth rate .. dependent changes in *Escherichia coli* membrane structure and protein leakage," Appl. Microbiol Biotechnol (2002) 58:386-392.
Shokri et al., "Characterisation of the *Escherichia coli* membrane structure and function during fedbatch cultivation," Microbial Cell Factories (2004) 3:9.
Harrison et al., "Factors Affecting the Fermentative Production of a lysozyme .. Binding Antibody Fragment in *Escherichia coli*," Biotechnology and Bioengineering (1997) 53: 611-622.
Chen et al., J. "Effect of Induction Conditions on Production and Excretion of *Aeromonas hydrophila* Chitinase by Recombinant*Escherichia coli*," J. of Fermentation and Bioengineering (1997) 84: 610-613.
Yee et al., "Recombinant Protein Expression in high cell density fed-batch cultures of *Escherichia coli*," Biotechnology (1992) 10:1550-1556.
Harrison et al., "Production of Antibody Fragments in *Escherichia coli*," Annals of New York Academy of Science (1996) 782:143-158.
Shin, C.S. et al., "Growth-associated synthesis of recombinant human glucagon and human growth hormone in high-cell-density cultures of *Escherichia coli*," Appl. Microbiol. Biotechnol. (1998) 49: 364-370.
Ryan et al., "Expression of --p .. lactamase by Recombinant *Escherichia coli* Strains Containing Plasmids of Different Sizes-Effects of pH, Phosphate, and Dissolved Oxygen," Biotechnology and Bioengineering (1989) 34: 309-319.
Zabriskie, D. et al., "Effects of fermentation feeding strategies prior to induction of expression of a recombinant malaria antigen in *Escherichia coli*," Microbiol. (1987).
Riesenberg, D. et al., "High cell density fermentation of recombinant *Escherichia coli* expressing human interferon alpha 1," App. Micro. Biotech. (1990).
Riesenberg, D. J., High cell density cultivation of *Escherichia coli* at controlled specific growth rateBiotechnol. (1991) 20: 17-28.
Kim, S. et al., "Effects of Growth Rate on the Production of Pseudomonas fluorescens Lipase during the Fed-Batch Cultivation of *Escherichia coli*," Biotech. Prog. (1996) 12: 718-722.
Jonasson, P. et al., "Genetic design for facilitated production and recovery of recombinant proteins in *Escherichia coli*Biotechnol" Appl. Biochem. (2002) 35: 91-105.
Miksch, G. et al., "The kil gene of the CoiE1 plasmid of *Escherichia coli* controlled by a growth-phase-dependent promoter mediates the secretion of a heterologous periplasmic protein during the stationary phase," Arch. Microbiol. (1997) 167: 143-150.
Fu et al., "Continuous, High Level Production and Excretion of a Plasmid-Encoded Protein by *Escherichia coli* in a Two-Stage Chemostat," Biotechnology and Bioengineering (1993) 41:937-946.

(Continued)

*Primary Examiner* — Kagnew H Gebreyesus
(74) *Attorney, Agent, or Firm* — McDonnell Boehnen Hulbert & Berghoff

(57) ABSTRACT

The present invention provides a method for controlling the partitioning of a recombinant protein between the supernatant and the periplasm in E. coli host cell cultures wherein expression of the recombinant protein by said cells is under the control of an inducible system, which method comprises: a) providing an E. coli host cell culture b) changing the growth rate of the E. coli host cells c) inducing expression of the recombinant protein wherein steps (b) and (c) can be performed in any order or simultaneously; and subsequently d) determining the yield of recombinant protein in the culture supernatant and the E. coli host cell periplasm e) comparing the yield determined in step (d) with the yield determined when at least one other growth rate has been used in step (b) f) selecting a growth rate from the comparison made in step (e) in which the partitioning of the recombinant protein between the supernatant and the periplasm is most suited to the primary recovery of the recombinant protein.

46 Claims, 6 Drawing Sheets

(56) References Cited

OTHER PUBLICATIONS

Figure 1:
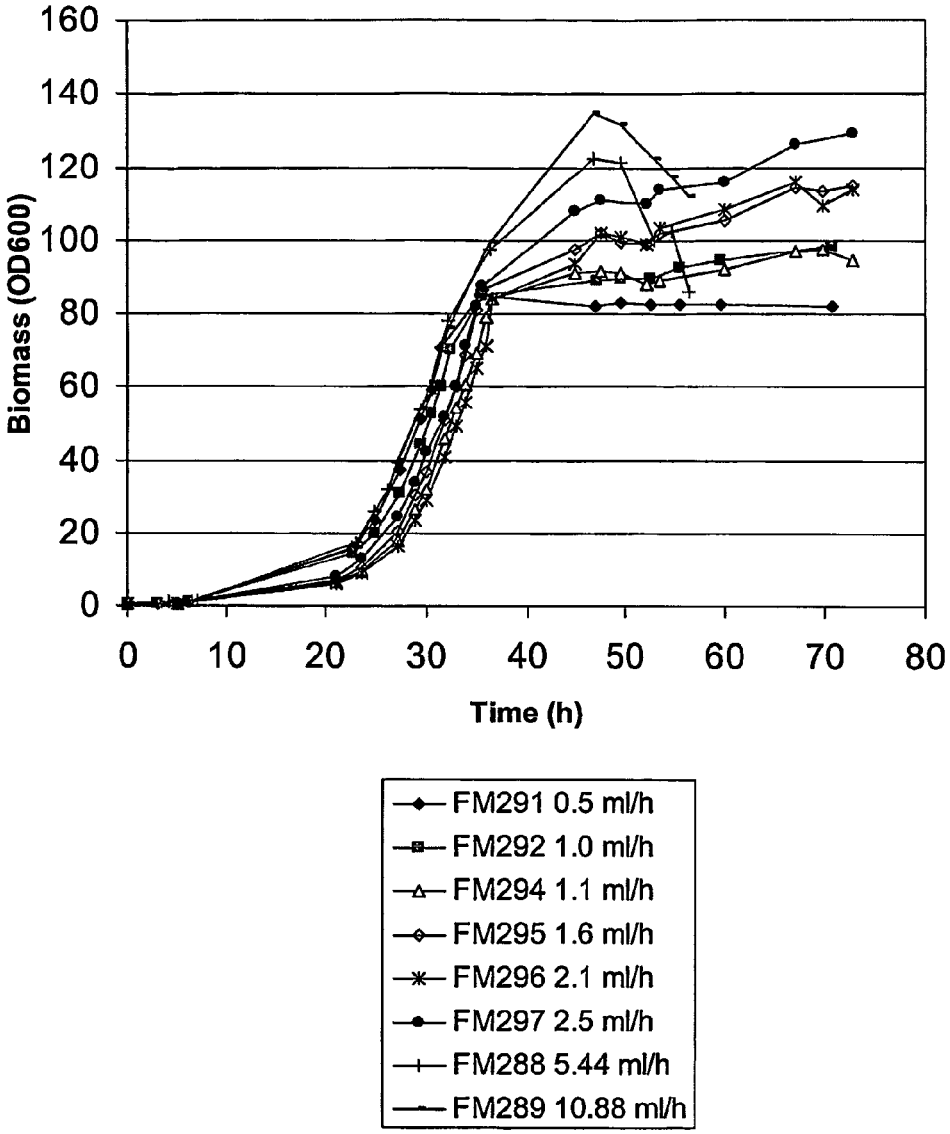

Chalmers, J. J. et al., "Effects of Temperature on *Escherichia coli* Overproducing 13-Lactamase or Human Epidermal Growth Factor," Applied and Environmental Microbiology (1990) 56:104-111.
Shibui, T. And Nagahari, K., "Secretion of a functional Fab fragment in *Escherichia coli* and the influence of culture conditions," Appl. Microbiol. Biotechnol. (1992) 37:352-357.
Donovan, R.S. et al., "Review: Optimizing inducer and culture conditions for expression of foreign proteins under the control of the lac promoter," J. of Industrial Microbiology (1996) 16: 145-154.
Shin, C.S. et al., "Synthesis of mini-proinsulin precursors using N-termini of-human TNF a as fusion partners in recombinant *Escherichia coli*," J. of Indus. Micro. & Biotech., (1999) 22:176-180.
EP1664278 Oppositions documents.
Shokri A. Growth rate-dependent changes in *Escherichia coli* membrane structure and protein leakage Applied Microbiology and Biotechnology (2002) 58:386-392.*
Korz et al,. Simple feed-batch technique for high cell density cultivation of *Escherichia coli,* Journal of Biotechnology, vol. 39, (1995) 59-65.*
Curless et al. Effect of Preinduction Specific Growth Rate on Secretion of Granulocyte Macrophage Colony Stimulating Factor by *Escherichia coli.* Biotechnol. Prog. 1994, 10, 467-471.*
Baneyx, F., "Recombinant protein expression in *Escherichia coli," Current Opinion in Biotechnology,* 1999, 10, 411-412.
Bird, R.E., et al., "Single-chain antigen-binding proteins," *Science,* 1988, 242, 423-242.
Goldstein, M.A., et al., "Prokaryotic promoters in biotechnology," *Buiotechnol. Annu. Rev.,* 1995, vol. 1, 105-128.
Harrison, J.S., et al., "Factors affecting the fermentative production of lysozyme-binding antibody fragment in *Escherichia coli," Biotechnology and Bioengineering,* 1997, 53(6), 611-622.
Humphreys, D.P., et al., "Therapeutic antibody production technologies: molecules, applications, expression and purification," *Current Opinion in Drug Discovery and Development,* 2001, 4, 172-185.
Humphreys, D.P., et al., "A plasmid system for optimization of Fab production in *Escherichia coli:* importance of balance of heavy chain and light chain synthesis," *Protein Expression & Purification,* 2002, 26, 309-320.
Kaderbhai, N., et al., "Glycine-induced extracellular secretion of a recombinant cytochrome expressed in *Escherichia coli," Biotechnology Applied Biochemistry,* 1997, 25(1), 53-61.
Lee, S.Y., "High cell-density culture of *Escherichia coli," Btech,* 1996, 14, 98-105.
Makrides, S.C., "Strategies for achieving high-level expression ofgenes in *Escherichia coli," Microbiological Reviews,* 1996, 60(3), 512-538.
Mountain, A., et al., "Engineering antibodies for therapy," *Biotechnol. Genet. Eng. Rev.,* 1992, 10, 1-142.
Orlandi, R., et al., "Cloning immunoglobulin variable domains for expression by the polymerase chain reaction," *Proc. Natl. Acad. Sci. USA,* 1989, 86, 3833-37.
Riechmann, L., et al., "Reshaping human antibodies for therapy," *Nature,* 1988, 322, 323-327.
Shokri, A., et al., "Growth rate-dependent changes in *Escherichia coli,* membrane structure and protein leakage," *Applied Microbiology Biotechnology,* 2002, 58, 386-392.
Simmons, L.C., et al., "Expression of full-length immunoglobulins in *Escherichia coli:* rapid and efficient production of aglycosylated antibodies," *J of Immunological Methods,* 2002, 263, 133-147.
Swartz, J.R., "Advances in *Escherichia coli* of therapeutic proteins," *Current Opinion in Biotechnology,* 2001, 12, 195-201.
Thiry, M., et al., "Optimizing scale-up fermentation processes," *Trends in Biotechnology,* 2002, 20(3), 103-105.
Verma R., et al., "Antibody engineering: comparison of bacterial, yeast, insect and mammalian expression systems," *J. of Immunological Methods,* 1998, 216, 165-181.
Ward, E.S., et al., "Binding activities of a repertoire of single immunoglobulin variable domains secreted from *Escherichia coli," Nature,* 1989, 341, 544.

* cited by examiner

METHODS FOR PRODUCING RECOMBINANT PROTEINS

Matter enclosed in heavy brackets [ ] appears in the original patent but forms no part of this reissue specification; matter printed in italics indicates the additions made by reissue.

BACKGROUND OF THE INVENTION

Field of the Invention

The present invention relates generally to methods for producing recombinant proteins in Escherichia coli host cell cultures and more specifically provides a method for controlling the partitioning of said proteins between the periplasm of E. coli host cells and the culture supernatant.

E. coli is a widely used and convenient system for the production of recombinant proteins. The advantages of this system comprise the ease of gene manipulation, the availability of reagents including gene expression vectors, the ease of producing quantities of protein, speed and the high adaptability of the system to express a wide variety of proteins. For review see Baneyx, Current Opinion in Biotechnology, 1999, 10, 411-421. E. coli is now widely used for the large-scale production of therapeutic proteins such as insulin, growth hormone and antibodies (Swartz, Current Opinion in Biotechnology, 2001, 12, 195-201; Humphreys and Glover, Current Opinion in Drug Discovery and Development, 2001, 4, 172-185; Verma et al., Journal of Immunological Methods, 1998, 216, 165-181; Simmons et al., Journal of Immunological Methods, 2002, 263, 133-147).

Expression of any foreign gene in E. coli begins with the insertion of a cDNA copy of the gene into an expression vector. Many forms of expression vector are available. Such vectors usually comprise a plasmid origin of DNA replication, an antibiotic selectable marker and a promoter and transcriptional terminator separated by a multi-cloning site (expression cassette) and a DNA sequence encoding at least one ribosome binding site. Transcription of the foreign gene is usually controlled by a regulated promoter, which allows cell growth to be separated from product synthesis resulting in higher yields than if the protein was constitutively expressed. Maximal yield of the protein can be achieved by determining the optimal point during fermentation for expression to be induced, typically once the cells have been grown to a high cell density.

Recombinant proteins expressed in E. coli can be produced in the cytoplasm, or secreted into the periplasm or the supernatant depending on the nature of the protein and its folding requirements (Makrides, Microbiological Reviews, 1996, 60, 512-538). For example, proteins can be targeted to the periplasm via a signal sequence and expression in the periplasm can offer several advantages over expression in the cytoplasm, including lower numbers of host cell proteins, less degradation of the recombinant protein and an oxidizing environment which facilitates proper protein folding.

While protein yield during fermentation is a key factor influencing the cost of producing recombinant proteins in E. coli, the cost of downstream processing (DSP) of the protein produced is also important in determining the final cost of goods. The term DSP encompasses all the steps following the fermentation of E. coli that result in the final purified functional protein. Depending on the cellular location of the recombinant protein produced, these steps may typically include primary recovery steps such as centrifugation, filtration, extraction and concentration/diafiltration steps followed by one or more purification steps. Maximising the efficiency of these steps to obtain a high yield of functional protein is key to minimizing costs during the large-scale production of recombinant proteins. The nature of the primary recovery steps used during DSP will affect the yield and quality of recombinant protein obtained and will depend on several factors including, the scale of production, the nature of the protein and its cellular location at the end of fermentation. For example, an important consideration for recombinant proteins produced in the periplasm is the level of leakage of the recombinant protein into the supernatant, as a natural level of leakage does occur during fermentation and this can have a detrimental effect on the yield and quality of the recombinant protein obtained from the periplasm. Where high levels of recombinant protein leak into the supernatant the viscosity of the supernatant increases, making primary recovery of the cells by centrifugation or filtration more difficult and therefore reducing the yield of protein obtained from the periplasm. The cells themselves are also less robust during centrifugation and are more likely to lyse resulting in damage to the protein and increasing the protein levels in the supernatant again reducing yield. An additional problem is that the quality of the protein recovered from the periplasm during extraction may also be reduced by contamination with recombinant protein from the supernatant that may not be correctly folded or may be partially degraded.

It is therefore desirable to improve the efficiency of primary recovery of recombinant proteins and hence to improve the final yield and quality of functional protein obtained by controlling the partitioning of recombinant proteins between the periplasm and the supernatant.

SUMMARY OF THE INVENTION

In the present invention, we have been able to demonstrate that it is possible to control the partitioning of recombinant proteins between the supernatant and the periplasm in E. coli host cell cultures by adjusting the growth rate of E. coli host cells. By selecting a suitable growth rate based on the partitioning of the protein between the supernatant and the periplasm and not necessarily on yield alone, the quality and/or yield of protein produced can be increased.

DETAILED DESCRIPTION OF THE INVENTION

Thus according to the present invention, there is provided a method for controlling the partitioning of a recombinant protein between the supernatant and the periplasm in E. coli host cell cultures wherein expression of the recombinant protein by said cells is under the control of an inducible system, which method comprises:

a) providing an E. coli host cell culture
b) changing the growth rate of the E. coli host cells
c) inducing expression of the recombinant protein wherein steps (b) and (c) can be performed in any order or simultaneously; and subsequently
d) determining the yield of recombinant protein in the culture supernatant and the E. coli host cell periplasm
e) comparing the yield determined in step (d) with the yield determined when at least one other growth rate has been used in step (b)
f) selecting a growth rate from the comparison made in step (e) in which the partitioning of the recombinant protein between the supernatant and the periplasm is most suited to the primary recovery of the recombinant protein.

The recombinant protein for use in the present invention may be any peptide, polypeptide or protein having more than about ten amino acids. The protein may be derived from any source including bacteria but more particularly from mammalian sources. In one example the recombinant protein is an antibody. The term 'antibody' as used herein refers to any immunoglobulin molecule from any class such as IgG, IgE, IgM, IgD and IgA for example a member of the IgG class e.g. IgG1 and also any antigen binding immunoglobulin fragment, such as Fv, Fab, Fab' and $F(ab')_2$ fragments, and any derivatives thereof, such as single chain Fv fragments. These antibodies and their fragments may be naturally occurring, humanized, chimeric or CDR grafted antibodies and standard molecular biology techniques may be used to modify, add or delete amino acids or domains as desired. The methods for creating these antibody molecules are well known in the art (see for example, Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

E. coli host cells for use in the present invention may be naturally occurring E. coli strains or mutated strains capable of producing recombinant proteins. Examples of specific host E. coli strains include MC4100, TG1, TG2, DHB4, DH5α, DH1, BL21, XL1Blue and JM109. Examples also include modified E. coli strains, for example metabolic mutants and protease deficient strains. One preferred E. coli host is E. coli W3110 (ATCC 27,325) a commonly used host strain for recombinant protein fermentations.

The recombinant protein of the present invention is typically expressed in either the periplasm of the E. coli host cells or the host cell culture supernatant, depending on the nature of the protein and the scale of production. The methods for targeting proteins to these compartments are well known in the art, for a review see Makrides, Microbiological Reviews, 1996, 60, 512-538. Examples of suitable signal sequences to direct proteins to the periplasm of E. coli include the E. coli PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelb leader, the protein A leader, the coexpression of bacteriocin release protein, the mitomycin-induced bacteriocin release protein along with the addition of glycine to the culture medium and the coexpression of the kil gene for membrane permeabilization.

In the present invention expression of the recombinant protein in the E. coli host cells is under the control of an inducible system. The term 'inducible system' as used herein refers to an inducible expression system whereby the expression of the recombinant protein in E. coli is under the control of an inducible promoter. Many inducible promoters suitable for use in E. coli are well known in the art and depending on the promoter, expression of the recombinant protein can be induced by varying factors such as temperature or the concentration of a particular substance in the growth medium (Baneyx, supra; Goldstein and Doi, 1995, Biotechnol. Annu. Rev, 105-128). Examples of inducible promoters include the E. coli lac, tac, and trc promoters which are inducible with lactose or the non-hydrolyzable lactose analog, isopropyl-β-D-1-thiogalactopyranoside (IPTG) and the phoA, trp and ara-BAD promoters which are induced by phosphate, tryptophan and L-arabinose respectively.

The term 'inducing expression' as used herein refers to the point at which induction is initiated, by for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

The E. coli host cell cultures of the present invention may be cultured in any medium that will support the growth of E. coli and expression of the recombinant protein. The medium may be any chemically defined medium, such as those provided in Pirt S. J. (1975) Principles of Microbe and Cell Cultivation, Blackwell Scientific Publications, with modifications where appropriate to control growth rate as described herein. An example of a suitable medium is 'SM6E' as described by Humphreys et al., 2002, Protein Expression and Purification, 26, 309-320.

Culturing of the E. coli host cells can take place in any suitable container such as a shake flask or a fermenter depending on the scale of production required. Various large scale fermenters are available with a capacity of greater than 1,000 liters up to about 100,000 liters. Preferably fermenters of 1,000 to 50,000 liters are used, more preferably 1,000 to 10,000 liters. Smaller scale fermenters may also be used with a capacity of between 0.5 and 1,000 liters.

Fermentation of E. coli may be performed in any suitable system, for example continuous, batch or fed-batch mode (Thiry and Cingolani, 2002, Trends in Biotechnology, 20, 103-105) depending on the protein and the yields required. Batch mode may be used with shot additions of nutrients or inducers where required. Alternatively, a fed-batch culture may be used and for example, the cultures grown in batch mode pre-induction at the maximum specific growth rate that can be sustained using the nutrients initially present in the fermenter and one or more nutrient feed regimes used to control the growth rate post-induction until fermentation is complete. Fed-batch mode may also be used pre-induction to control the metabolism of the E. coli host cells and to allow higher cell densities to be reached (Lee, 1996, Tibtech, 14, 98-105).

In the present invention the cells are grown at any suitable growth rate prior to induction of protein expression. To achieve high growth rate E. coli host cells are typically grown in cultures where the nutrient levels, carbon source, temperature and oxygen conditions permit such growth. Preferably the E. coli host cells in the present invention are grown under nutrient unlimited conditions at high growth rate to obtain a high cell density prior to induction of recombinant protein expression. Growth can be measured in several different ways the most common of which is to measure the increase in cell density by measuring the increase in optical density at 600 nm over time. The specific growth rate can be determined by plotting the natural logarithm of the $OD_{600}$ measurements versus time. Growth measurements can be taken throughout the culture, for example, by on line measurement or by taking samples from the cultures at regular time intervals during fermentation. Preferably a high cell density is obtained before expression of the recombinant protein is induced. Examples of suitable densities at which protein expression may be induced range from about 60 to about 100 $OD_{600}$.

In step (b) of the method of the present invention the growth rate is changed compared to the growth rate in the E. coli cultures provided in step (a) of the method. The change in growth rate in step (b) may take place at any time before induction of protein expression in step (c), at the same time as induction of protein expression or after induction of protein expression. In one example, where the growth rate is changed before step (c) the cultures are grown at high growth rate in step (a) of the method until a high cell density is reached after which the growth rate is changed and protein expression induced once the desired growth rate change has been observed. In one such example the growth rate is changed at between about 1 and about 3 hours before induction of protein expression. In another example the cultures are grown at high growth rate in step (a) of the method and protein expression is induced in step (c) of the method, after which the growth rate is changed in step (b) of the method. In one such example the growth rate is changed at between about 1 and about 3 hours after step (c). In another example the cells are grown at high growth rate in step (a) of the method and steps (b) and (c) take place simultaneously, i.e. at approximately the same time such that the growth rate is changed at the point of induction.

The growth rate of the E. coli host cells may be controlled by many different methods well known in the art depending on the fermentation system (See for example Lee 1996, Tibtech, 14, 98-105). Suitable methods for controlling growth rate include changes in temperature, available oxygen levels and nutrient levels. Appropriate temperature changes, oxygen levels or concentrations of nutrients required to achieve a specific growth rate can be determined empirically by one skilled in the art by testing a range of concentrations and measuring the effect on growth rate. In one example, the concentration of nutrients such as nitrogen and phosphate present at the start of the fermentation can be used to control the growth rate depending on the point during induction at which the nutrient is depleted. In one particular example of the present invention the nutrient source controlling growth rate is phosphate. Suitable phosphate concentrations are provided in the examples herein and are known in the art (See for example, Pirt, S. J. (1975) Principles of Microbe and Cell Cultivation, Blackwell Scientific Publications). Examples of suitable phosphate concentrations present in the starting fermentation include those in the range of 25 to 40 mM. Hence in one example of the present invention the growth rate in step (b) is changed by adjusting the level of phosphate available to the cells at the start of fermentation. In another example the growth rate may be adjusted by changing the concentration of nutrients such as carbon or nitrogen added to the culture for example via a feed or through shot additions.

In another example of the present invention, the growth rate in step (b). is changed by adjusting the level of carbon available to the E. coli host cells. The level of carbon source available to the cells may be increased or decreased to achieve the required change in growth rate. Preferably the growth rate is controlled by adjusting the feed rate of carbon source into the culture. The term 'carbon source' as used herein refers to the carbon source that is available as an energy source for E. coli during growth and includes sugars such as glucose, lactose, sucrose and fructose and other carbon sources such as glycerol, succinate and lactate. In a preferred embodiment of the present invention the carbon source is glycerol. Preferably the host cells are cultured in a fed-batch fermenter and the carbon source is glycerol provided at a suitable feed rate to provide the required growth rate. Suitable glycerol feed rates are well known in the art and include those described in the examples provided herein. Examples of suitable glycerol feed rates include those in the range of from 0.5 to 11 ml/h.

The term 'partitioning' as used herein refers to the distribution of recombinant protein between the periplasm of E. coli host cells and the supernatant in which they are grown. To determine the partitioning of the recombinant protein the yield in the periplasm and the supernatant is determined in step (d) of the method. The yield may be determined by taking samples at suitable time intervals throughout the culture of the E. coli host cells, for example about every 2-4 hours, or alternatively at the point of harvest, for example about 24 to 36 hours after induction. Many methods of protein quantification are known in the art and include methods such as gel electrophoresis, HPLC, chromatography and immunodetection methods such as western blots and ELISA. For example, Fab' concentrations in periplasmic extracts and culture supernatants can be determined by Fab' assembly ELISA as described in Humphreys et al., 2002, Protein Expression and Purification, 26, 309-320.

In the method of the present invention the yield of recombinant protein in the supernatant and the periplasm of E. coli host cells grown at two or more different growth rates in step (b) are compared in step (e) of the method in order to find the growth rate which results in partitioning that is most suited to the primary recovery of the protein product. Preferably the yields compared in step (e) are determined in step (d) at approximately the same time after induction for each growth rate. It will be appreciated that this may not always be possible, especially for cultures grown at higher growth rates where the maximum biomass is reached earlier than in cultures grown at lower growth rates.

The growth rate change in step (b) of the method may be an increase or a decrease in growth rate. The culture provided in step (a) may be growing at any suitable growth rate in either nutrient unlimited or nutrient limited conditions. Preferably the culture provided in step (a) is growing in nutrient unlimited conditions at the maximum specific growth rate possible in those conditions. In one example the growth rate of the E. coli host cells in step (a) is between about 0.1 and 0.25/h, preferably between 0.13 and 0.22/h. Preferably the growth rate is reduced in step (b) of the method. The growth rate may be reduced to any suitable rate above 0/h, preferably between 0/h and the growth rate provided in step (a). Suitable growth rates may be identified empirically by testing at least two different growth rates and comparing them in step (e) of the method. Each growth rate may be tested in two or more separate cultures grown in parallel and/or in succession. In one example at least two cultures are grown simultaneously using a different growth rate in each culture in step (b). In another example at least two cultures are grown sequentially using a different growth rate in each culture in step (b). Alternatively two or more different growth rates may be tested in a single culture by carrying out steps (a) to (d) using one growth rate in step (b) and then carrying out steps (b) and (d) at least once more varying the growth rate in step (b) each time. It will be appreciated that if no suitable growth rate is identified in step (e) of the method then further growth rates may be tested by repeating steps (a) to (d) of the method. Typically a range of different growth rates will be tested between 0/h and the growth rate of the cultures in step (a). In the first instance the range of different growth rates tested may span a wide range of high and low growth rates that may be subsequently narrowed if required by repeating steps (a) to (d) of the method using a narrower range of growth rates in step (b). Suitable growth rates for testing in the first instance may for example be between about 2 and about 200 fold less than the growth rate in nutrient unlimited conditions. In one example the growth rate is between about 5 and about 200 fold less than the growth rate in nutrient unlimited conditions.

Alternatively, in the first instance the range of different growth rates tested may be a narrow range for example of high or low growth rates that may be subsequently widened if required by repeating steps (a) to (d) of the method using a wider range of growth rates in step (b). Suitable growth rates for testing in the first instance may be for example between about 2 and about 50 fold less than the growth rate in nutrient unlimited conditions or between about 100 and about 200 fold less. In one example the growth rate is between about 5 and about 20 fold less than the growth rate in nutrient unlimited conditions. Suitable growth rates in step (b) may include growth rates in the range of 0.0005 to 0.04/h.

Once the partitioning of the recombinant protein at two or more different growth rates has been compared the growth rate most suited to the primary recovery of the recombinant protein is selected in step (f) of the method. The term 'primary recovery' as used herein refers to the initial recovery steps required to produce a cell free supernatant or periplasmic extract suitable for subsequent purification steps. Examples of primary recovery steps include, centrifugation, filtration, cell extraction or lysis, homogenisation, concentration, diafiltration and expanded bed adsorption. The growth rate most suited to the primary recovery of the protein will be the growth rate that results in the best yield and/or quality of protein following one or more primary recovery steps. The term 'quality' as used herein refers to the integrity of the protein obtained, whether it is intact and/or correctly folded. Importantly the most suitable growth rate may not be the growth rate that results in the maximum yield of recombinant protein in the E. coli host cell culture but may instead be the growth rate that results in the best partitioning of the protein between the periplasm and the supernatant which will result in better quality protein and/or higher yields following one or more primary recovery steps. Hence the growth rate selected in step (f) may be a trade off between the protein yield during culture and the final yield and quality of protein ultimately recovered.

In one example the recombinant protein may be expressed in the periplasm of E. coli host cells as these are easier to handle at large-scale than the supernatant. The first primary recovery step required is the recovery of the host cells from the culture medium, either by centrifugation or filtration. For proteins produced in the periplasm an important consideration is the level of leakage of the recombinant protein into the supernatant as this can have a detrimental effect on the primary recovery and quality of the periplasmic protein. The increased protein present in the supernatant increases the viscosity of the supernatant making recovery of the cells by centrifugation or filtration more difficult and reducing periplasmic protein yield. The cells themselves are also less robust during centrifugation and are more likely to lyse resulting in damage to the recombinant protein and further increasing the viscosity of the supernatant due to release of protein, DNA and lipids, which again reduces the yield of recombinant protein in the periplasm. The quality of the recombinant protein recovered from the periplasm may also be reduced by contamination with recombinant protein from the supernatant that may be partially degraded or not correctly folded. In these cultures it is important therefore to keep levels of recombinant protein low in the supernatant to increase the quality and/or yield of recombinant protein following primary recovery. In this example the final yield and/or quality of the recombinant protein obtained following primary recovery may be improved by selecting a growth rate where the level of recombinant protein in the supernatant is low even if the yield of recombinant protein in the periplasm is lower than at other growth rates where the levels of recombinant protein in the supernatant are higher. Therefore, for proteins produced in the periplasm in the method of the present invention it is preferred that the growth rate selected in step (f) is a growth rate at which greater than 55% of the protein is expressed in the periplasm and less than 45% of the protein is in the supernatant. Preferably greater than 80% of the protein produced by the host cells is expressed in the periplasm and less than 20% is in the supernatant. In one example greater than 90% of the protein produced by the host cells is expressed in the periplasm and less than 10% is in the supernatant. In another example greater than 95% of the protein produced by the host cells is expressed in the periplasm and less than 5% is in the supernatant.

In another example the protein may be produced in the supernatant. The protein may be easier to purify given that no extraction step is required and there will be fewer host proteins present in the medium. The quality of protein may also be better as there will be less proteolysis and there may be improved protein folding. For proteins produced in the supernatant it is important that the amount of recombinant protein expressed by the host cells and secreted to the supernatant is maximized. To determine if all the recombinant protein produced by the host cells is being secreted into the supernatant it is important to measure the recombinant protein levels in the periplasm as well. If these are still high it may be possible using the method of the present invention to adjust the partitioning of the recombinant protein to increase the yield in the supernatant still further. As a result, for proteins produced in the supernatant in the method of the present invention it is preferred that the growth rate selected in step (f) is a growth rate at which greater than 55% of the protein is expressed in the supernatant and less than 45% of the protein is in the periplasm. Preferably greater than 80% of the recombinant protein produced by the host cells is produced in the supernatant and less than 20% in the periplasm. In one example greater than 90% of the protein produced by the host cells is in the supernatant and less than 10% is in the periplasm. In another example greater than 95% of the protein produced by the host cells is in the supernatant and less than 5% is in the periplasm.

Having identified a suitable growth rate in step (f) of the method, the same growth rate can be used during subsequent fermentations of the E. coli host cells to ensure the desired partitioning of the recombinant protein between the supernatant and the periplasm is achieved. The present invention therefore also provides a method of producing a recombinant protein in E. coli host cell cultures wherein expression of the recombinant protein by said cells is under the control of an inducible system and the partitioning of the recombinant protein between the supernatant and the periplasm is most suited to the primary recovery of the recombinant protein said method comprising growing the E. coli host cells at the growth rate selected in step (f) of the method described above. These subsequent fermentations may be at the same scale or a different scale to that used in the method described above. For example the E. coli host cells may be fermented at a small scale to determine the growth rate most suited to the primary recovery of the protein and then in subsequent fermentations the host cells may be fermented at large scale to produce larger quantities of the recombinant protein using the growth rate selected in step (f).

The recombinant protein produced by the method of the present invention may be subsequently purified following primary recovery. The primary recovery steps used will depend on the cellular location of the recombinant protein at the end of the fermentation. For example, proteins expressed in the periplasm may be recovered within the host cells by centrifugation or filtration. The protein can then be extracted from within the cells using methods such as heat treatment (see for example U.S. Pat. No. 5,665,866) or mechanical extraction. Proteins expressed in the supernatant may be recovered using methods such as expanded-bed adsorption or centrifugation or filtration to remove cells followed by for example ion exchange or affinity chromatography to capture the protein. The protein from either the periplasmic extract or the supernatant may subsequently be purified using any of the methods known in the art depending on the nature of the recombinant protein and its physical properties such as size, hydrophobicity and isoelectric point. Such methods may include, size exclusion chromatography, hydrophobic interaction chromatography, ion exchange, affinity chromatography and reverse phase BPLC. Thus in another aspect of the present invention there is provided a method of producing a recombinant protein in E. coli host cell cultures wherein expression of the recombinant protein by said cells is under the control of an inducible system and the partitioning of the recombinant protein between the supernatant and the periplasm is most suited to the primary recovery of the recombinant protein said method comprising growing the E. coli host cells at the growth rate selected in step (f) of the method described above and subsequently purifying the recombinant protein.

EXAMPLES AND BRIEF DESCRIPTION OF THE FIGS.

The present invention will now be described by way of example only, in which reference is made to:

FIG. 1 Growth profile of E. coli at a range of glycerol feeding rates

Figure 2:
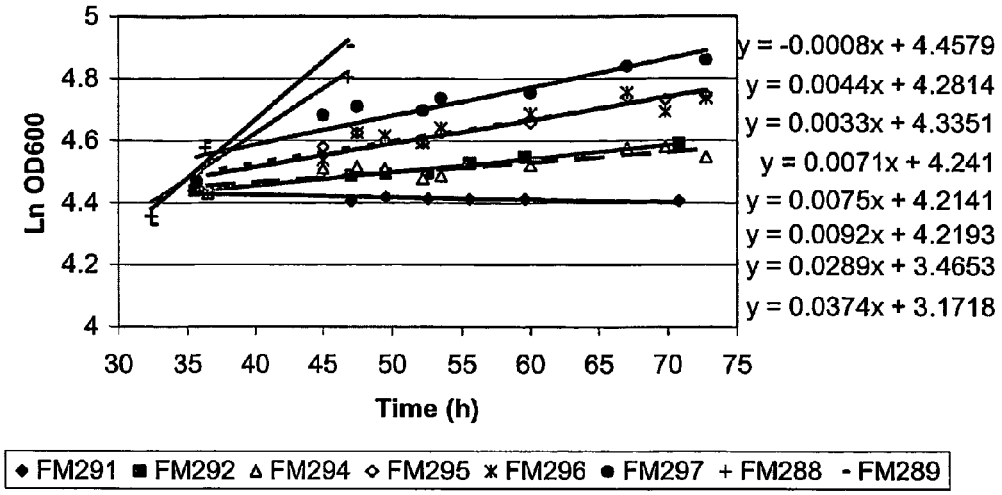
Figure 3:
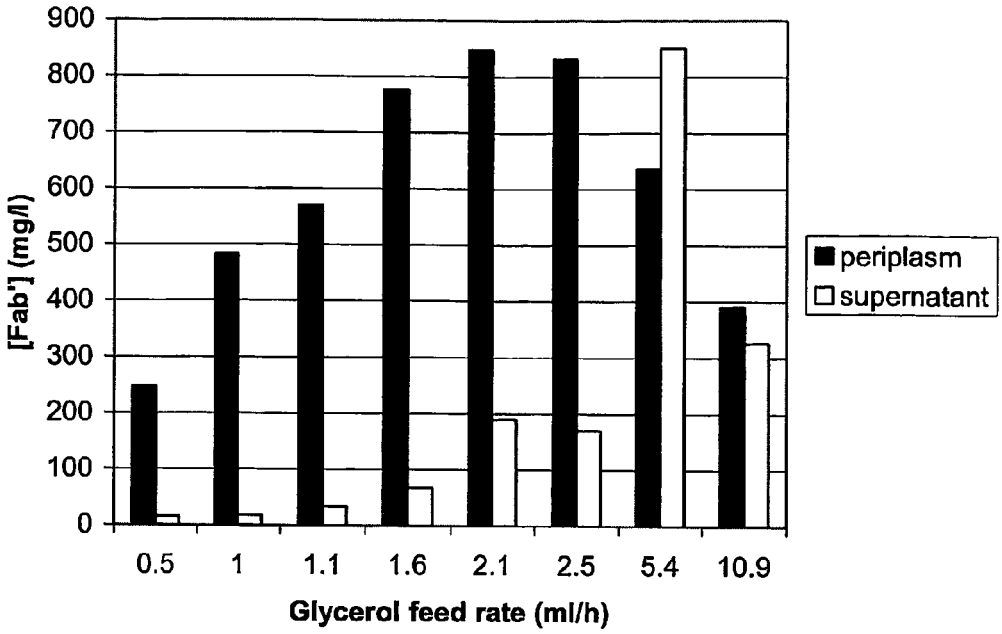
Figure 4:
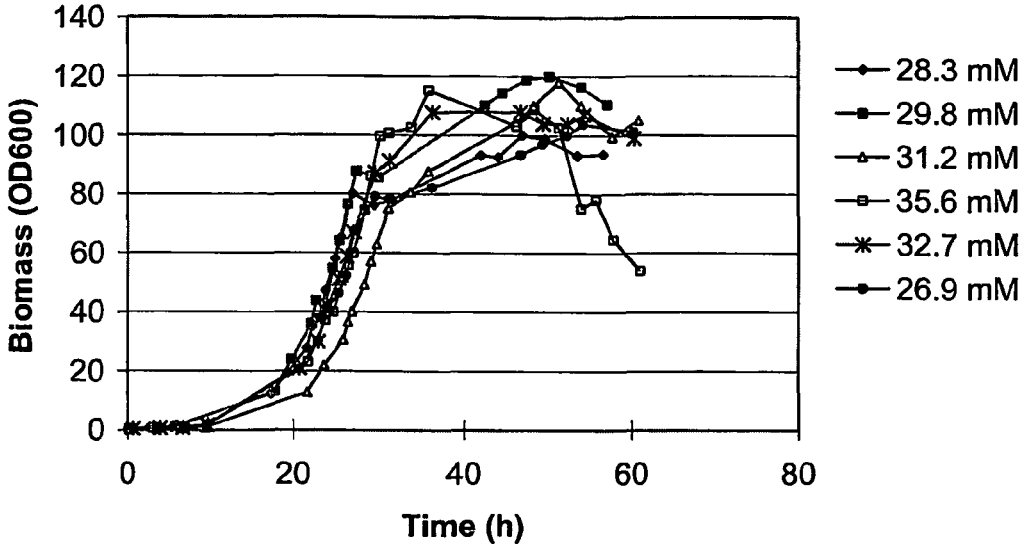
Figure 5:
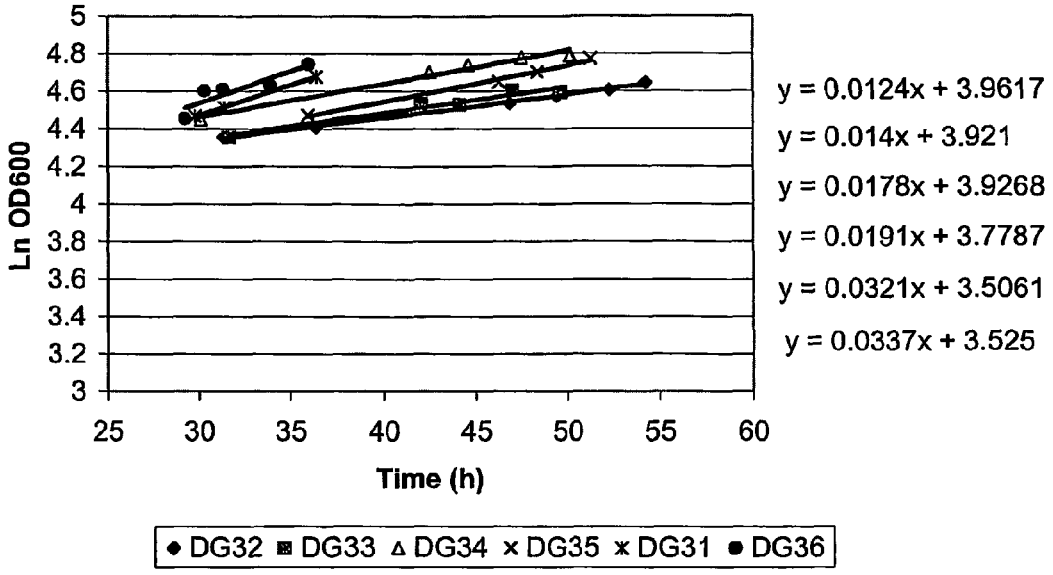
Figure 6:
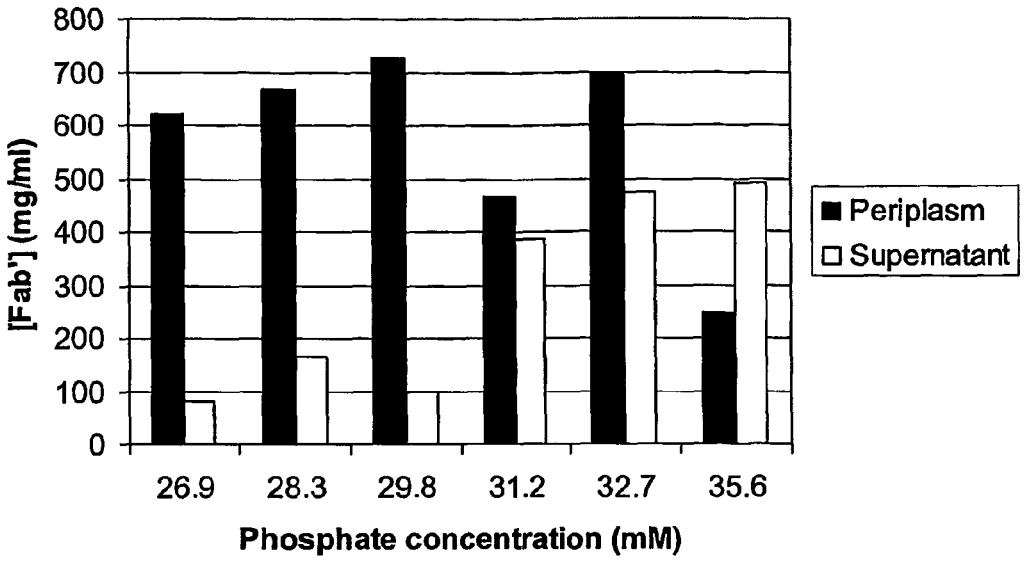

FIG. 2 Post-induction growth rate of E. coli at a range of glycerol feed rates FIG. 3 Partitioning of Fab'A between the periplasm and the supernatant in E. coli cultures grown at a range of glycerol feed rates FIG. 4 Growth profile of E. coli at a range of inorganic phosphate concentrations FIG. 5 Post-induction growth rate of E. coli at a range of inorganic phosphate concentrations FIG. 6 Partitioning of Fab'B between the periplasm and the supernatant in E. coli cultures grown at a range of inorganic phosphate concentrations

EXAMPLE 1

Optimisation of partitioning and yield of Fab'A using a limiting glycerol feed to control post-induction growth.

Materials and Methods

Strain and plasmid. The strain used in this work was Escherichia coli W3110 (ATCC 27325) transformed with a plasmid which confers resistance to tetracycline and carries genes coding for the light and heavy chain polypeptide components of the Fab' fragment, Fab'A. Each polypeptide is preceded by the E. coli OmpA leader peptide. Induction of expression from a single tac promoter results in synthesis and secretion of light and heavy chain polypeptides into the periplasm where a portion of the polypeptides fold and assemble to form Fab'.

Growth Medium

The fermentation growth medium was based on SM6E medium (described in Humphreys et al., 2002, Protein Expression and Purification, 26, 309-320) with 3.86 g/l $NaH_2PO_4.H_2O$ and 112 g/l glycerol.

Inoculum. Inoculum cultures were grown in the same medium supplemented with 10 μg/ml tetracycline. Cultures were incubated at 30° C. with agitation for approximately 22 hours.

Fermentation. Fermenters (2.5 liters total volume) were seeded with inoculum culture to 0.3-0.5 $OD_{600}$. Temperature was maintained at 30° C. during the growth phase and was reduced to 25° C. prior to induction. The dissolved oxygen concentration was maintained above 30% air saturation by variable agitation and airflow. Culture pH was controlled at 7.0 by automatic titration with 15% (v/v) $NH_4OH$ and 10% (v/v) conc. $H_2SO_4$. Foaming was controlled by the addition of 10% (v/v) Struktol J673 solution (Schill and Seilacher). A number of additions were made at different stages of the fermentation. When biomass concentration reached approximately 40 $OD_{600}$, magnesium salts and $NaH_2PO_4.H_2O$ were added. Further additions of $NaH_2PO_4.H_2O$ were made prior to and during the induction phase to ensure phosphate was maintained in excess. When the glycerol present at the beginning of fermentation had depleted (approximately 75 $OD_{600}$) a continuous feed of 80% (w/w) glycerol was applied at rates ranging from 0.5 to 10.9 ml/h. At the same point in the fermentation an IPTG feed was applied at a rate of 1 ml/h for 36 hours such that the final concentration of IPTG in the fermenter at this time point was 0.5 mM. The start of IPTG feeding was taken as the start of induction. Fermentations were typically run for 70-73 hours at the lower glycerol feed rates (0.5-2.5 ml/h) and 50-60 h at the higher glycerol feed rates (5.4-10.9 ml/h).

Measurement of biomass concentration and growth rate. Biomass concentration was determined by measuring the optical density of cultures at 600 nm. Growth rate (μ) is related to the change in biomass concentration over time thus:

$$LnX_t = LnX_0 + \mu t$$

where $X_o$ is the original biomass concentration, $X_t$ is the biomass concentration after time interval, t. Thus, a plot of $LnX_t$ against t for a batch culture gives a straight line of slope equal to μ (unit per hour). However, the application of a linear limiting feed of glycerol to a batch culture results in a decreasing growth rate due to the increases in biomass and culture volume. Therefore, an average growth rate during the induction period was determined by plotting $LnOD_{600}$ against time. The slope of a line of best fit (by the least squares method) was determined to give the average growth rate over the feed period.

Periplasmic Extraction. Cells were collected from culture samples by centrifugation. The supernatant fraction was retained (at −20° C.) for further analysis. The cell pellet fraction was resuspended to the original culture volume in extraction buffer (100 mM Tris-HCl, 10 mM EDTA; pH 7.4). Following incubation at 60° C. for approximately 16 hours the extract was clarified by centrifugation and the supernatant fraction retained (at −20° C.) for analysis.

Fab' quantification. Fab' concentrations in periplasmic extracts and culture supernatants were determined by Fab' assembly ELISA as described in Humphreys et al., 2002, Protein Expression and Purification, 26, 309-320.

Results

Fab'A fermentations were run under conditions where growth was unlimited pre-induction and growth occurred at the maximum specific rate ($\mu_{max}$) but was subsequently restricted post-induction (FIG. 1). Growth rate post-induction was controlled by the application of a nutrient (glycerol) limiting feed to the batch culture at a range of flow rates. Glycerol flow rates were selected to give a range of growth rates upwards of approximately 0/h. FIG. 2 and Table 1 show the actual average growth rate over the induction period for a range of glycerol feed rates. Increasing the glycerol feed rate resulted in an increase in the average growth rate of the culture as intended.

TABLE 1

Average growth rates of *E. coli* cultures grown at a range of glycerol feed rates.

| Culture | Feed rate (ml/h) | Growth rate/h |
|---|---|---|
| FM291 | 0.5 | −0.0008 |
| FM292 | 1.0 | 0.0044 |
| FM294 | 1.1 | 0.0033 |
| FM295 | 1.6 | 0.0071 |
| FM296 | 2.1 | 0.0075 |
| FM297 | 2.5 | 0.0092 |
| FM288 | 5.44 | 0.0289 |
| FM289 | 10.88 | 0.0374 |

Fermentations were harvested at approximately 36 hours post-induction at the lower glycerol feed rates (0.5-2.5 ml/h) and at about 24 hours post-induction at the higher glycerol feed rates (5.4-10.9 ml/h) and the Fab' concentration in periplasmic extracts and culture supernatants determined by Fab' assembly ELISA. FIG. 3 shows the Fab' concentration and relative distribution between the periplasm and culture medium. An optimal growth rate for Fab' titre was found to be approximately 0.0075/h. A general trend was observed in which the Fab' titre in the culture supernatant increased with increasing growth rate. Thus the growth rate selected for optimal fermentation performance, Fab' yield and compatibility with primary recovery will reflect a balance between maximum yield and optimal distribution of Fab'. In the cited example, a glycerol feed rate of 1.6 ml/h (growth rate ~0.0071/h) was selected for fermentation scale-up.

EXAMPLE 2

Optimisation of partitioning and yield of Fab'B by varying phosphate concentration to control post-induction growth rate Materials and Methods Strain and plasmid. The strain used in this work was Escherichia coli W3110 (ATCC 27325) transformed with a plasmid which confers resistance to tetracycline and carries genes coding for the light and heavy chain polypeptide components of the Fab' fragment, Fab'B. Induction of expression from a single tac promoter results in synthesis and secretion of light and heavy chain polypeptides into the periplasm where a portion of the polypeptides fold and assemble to form Fab'.

Growth Media

The fermentation growth medium was based on SM6E medium (described in Humphreys et al., 2002, Protein Expression and Purification, 26, 309-320) with the $NaH_2PO_4.H_2O$ concentrations given in Table 2.

TABLE 2

Amount and concentration of $NaH_2PO_4 \bullet H_2O$ used in Fab'B fermentations

| Fermentation batch number | $NaH_2PO_4 \bullet H_2O$ added (g/l) | Concentration of $NaH_2PO_4 \bullet H_2O$ (mM) |
|---|---|---|
| DG32 | 3.71 | 26.9 |
| DG33 | 3.91 | 28.3 |

TABLE 2-continued

Amount and concentration of $NaH_2PO_4 \bullet H_2O$ used in Fab'B fermentations

| Fermentation batch number | $NaH_2PO_4 \bullet H_2O$ added (g/l) | Concentration of $NaH_2PO_4 \bullet H_2O$ (mM) |
|---|---|---|
| DG34 | 4.11 | 29.8 |
| DG35 | 4.31 | 31.2 |
| DG31 | 4.52 | 32.7 |
| DG36 | 4.91 | 35.6 |

Inoculum. Inoculum cultures were grown in the same medium with the appropriate concentration of $NaH_2PO_4.H_2O$ (see Table 2) and supplemented with 10 μg/ml tetracycline. Cultures were incubated at 30° C. with agitation for approximately 19-26 hours.

Fermentation. Fermenters (2.5 liters total volume) were seeded with inoculum culture to 0.3-0.5 $OD_{600}$. Temperature was maintained at 30° C. during the growth phase and was reduced to 27° C. prior to induction. The dissolved oxygen concentration was maintained above 30% air saturation by variable agitation and airflow. Culture pH was controlled at 7.0 by automatic titration with 15% (v/v) $NH_4OH$ and 10% (v/v) conc. $H_2SO_4$. Foaming was controlled by the addition of 10% (v/v) Mazu solution.

A number of additions were made at different stages of the fermentation. Glycerol was added to the fermentation as 2×45 ml aliquots of an 80% (w/w) solution, one addition at a biomass concentration of 20 $OD_{600}$ and the other at 40 $OD_{600}$. When biomass concentration reached approximately 40 $OD_{600}$ magnesium and calcium salts were also added. Lactose (60 ml of a 50% (w/w) solution) was added at 60 $OD_{600}$ and served as an inducer and carbon source during the induction phase. Induction occurred upon glycerol depletion (between about 75 and 90 $OD_{600}$) as marked by an increase in dissolved oxygen concentration. Further additions of lactose were made as required to maintain the concentration in the fermenter between 0 and 55 g/l. A further addition of magnesium was made between 0 and 2 hours post-induction. Fermentations were typically run for 56-61 hours.

Analysis of fermentations. Periplasmic extractions, measurement of biomass and quantification of Fab' were done as described previously (Example 1).

Results

The growth of fermentation cultures post-induction was controlled by varying the amount of phosphate ($NaH_2PO_4.H_2O$) whilst keeping all other starting nutrients constant (FIG. 4). The growth rate during each fermentation was determined for the period of induction in which biomass increased (FIG. 5 and Table 3).

TABLE 3

Average growth rates of *E. coli* cultures grown at a range of phosphate concentrations.

| Fermentation Batch number | Phosphate concentration mM | Growth rate/h |
|---|---|---|
| DG32 | 26.9 | 0.0124 |
| DG33 | 28.3 | 0.014 |
| DG34 | 29.8 | 0.0178 |
| DG35 | 31.2 | 0.0191 |
| DG31 | 32.7 | 0.0321 |
| DG36 | 35.6 | 0.0337 |

Increasing the phosphate concentration resulted in an increase in growth rate over these periods of induction. The phosphate concentrations were selected to deplete at various points relative to induction (slightly before induction, e.g. 26.9 mM, to various points after induction). The point (biomass concentration) at which induction occurs is related to the starting glycerol concentration. The amount of phosphate required to support growth to the desired induction biomass was calculated based on biomass yield coefficient data for inorganic phosphate provided in Pirt, S. J. (1975) Principles of Microbe and Cell Cultivation, Blackwell Scientific Publications. The optimal phosphate concentration for Fab' yield and distribution was determined empirically as described herein. Fermentations were harvested 28-31 hours post-induction and the Fab' concentration in periplasmic extracts and culture supernatants determined by Fab' assembly ELISA. FIG. 6 shows the Fab' concentration in both the periplasm and culture supernatant at harvest. A general trend was observed in which the Fab' concentration in the culture supernatant increased with phosphate concentration. The optimal range of phosphate for large scale primary recovery using periplasmic extraction and centrifugation / filtration methods was 29.8 mM.

The invention claimed is:

1. A method for determining the growth rate of E. coli host cells that [results in partitioning of a recombinant protein produced by the host cells between the periplasm of the host cells and the supernatant of the culture medium in which the cells are grown that is most suited to the primary recovery of the recombinant protein, wherein expression of the recombinant protein by said cells is under the control of an inducible system, which method comprises:] *facilitates primary recovery of recombinant protein from the supernatant, the method comprising,* a) providing an E. coli host cell culture*;* b) changing the growth rate of the E. coli host cells such that the growth rate is in the range of 0.0005 to 0.04/h*;* c) inducing expression of the recombinant protein *under the control of an inducible system* wherein steps (b) and (c) are performed in any order or simultaneously; [and subsequently]

d) determining the yield of recombinant protein in the supernatant of the culture medium and the E. coli host cell periplasm*;* e) performing steps (b) and (d), and optionally steps (a) and (c), using a growth rate different from the growth rate initially used in step (b)*;* f) comparing the yield determined in step (d) with the yield determined in step (e); and g) selecting a growth rate from the comparison made in step (f) [, the selected growth rate being in the range of 0.0005 to 0.0092/h, the selected growth rate being most suited to the primary recovery of the recombinant protein from the supernatant.]*;*

*wherein the growth rate is in the range of 0.0005 to 0.0092/h.*

2. The method according to claim 1 wherein the yields compared in step (f) are from at least two cultures grown simultaneously.

3. The method according to claim 1 wherein the yields compared in step (f) are from at least two cultures grown sequentially.

4. The method according to claim 1 wherein the yields compared in step (f) are from one culture grown at at least two different growth rates by carrying out steps (a) to (d) using one growth rate in step (b) and then carrying out steps (b) and (d) at least once more varying the growth rate in step (b) each time.

5. The method according to claim 1 wherein the growth rate in step (b) is reduced.

6. The method according to claim 1 wherein changing the growth rate of the E. coli host cells in step (b) comprises adjusting the level of carbon available to the cells.

7. The method according to claim 6 wherein the carbon source is selected from glucose, lactose, sucrose, fructose, glycerol, succinate and lactate.

8. The method according to claim 7 wherein the carbon source is glycerol.

9. The method according to claim 1 wherein changing the growth rate of the E. coli host cells in step (b) comprises adjusting the level of phosphate available to the cells.

10. The method according to claim 1 wherein changing the growth rate of the E. coli host cells in step (b) comprises adjusting the level of oxygen available to the cells.

11. The method according to claim 1 wherein the recombinant protein is targeted to the periplasm.

12. The method according to claim 11 wherein the growth rate selected in step (g) is a growth rate at which greater than 80% of the recombinant protein produced by the host cells is expressed in the periplasm.

13. The method according to claim 1 wherein the recombinant protein is targeted to the supernatant.

14. The method according to claim 13 where wherein the growth rate selected in step (g) is a growth rate at which greater than 80% of the recombinant protein produced by the host cells is produced in the supernatant.

15. The method according to claim 1 wherein the inducible system comprises a lac derived promoter.

16. The method according to claim 15 wherein the lac derived promoter is lac, tac or trc.

17. The method according to claim 15 wherein the promoter is induced with lactose or IPTG.

18. The method according to claim 1 wherein the recombinant protein is an antibody or fragment thereof.

19. The method according to claim 18 wherein the recombinant protein is an antibody that is an IgG.

20. The method according to claim 18 wherein the recombinant protein is an antibody fragment that is a Fab, Fab', $F(ab')_2$ or scFv.

21. A method of producing a recombinant protein in E. coli host cells wherein [expression of the recombinant protein by said cells is under the control of an inducible system and the partitioning of the recombinant protein between the supernatant of the culture medium in which the cells are grown and the periplasm of the host cells is most suited to the primary recovery of the recombinant protein said method] *primary recovery of the protein is from the supernatant, the method* comprising, a) providing an E. coli host cell culture*;* b) changing the growth rate of the E. coli host cells such that the growth rate is in the range of 0.0005 to 0.04/h*;* c) inducing expression of the recombinant protein under the control of an inducible system wherein steps (b) and (c) are performed in any order or simultaneously; [and subsequently]

d) determining the yield of recombinant protein in the supernatant of the culture medium and the E. coli host cell periplasm*;* e) performing steps (b) and (d), and optionally steps (a) and (c), using a growth rate different from the growth rate initially used in step (b)*;* f) comparing the yield determined in step (d) with the yield determined in step (e)*;* g) selecting a growth rate in the range of 0.0005 to 0.0092/h from the comparison made in step (f) [the selected growth rate being most suited to the primary recovery of the recombinant protein from the supernatant]; and h) growing the E. coli host cells at the growth rate selected in step (g).

22. The method according to claim 21 wherein the recombinant protein produced is subsequently purified.

23. The method of claim 21 wherein E. coli host cells are grown in a phosphate concentration in the range of 26.9 to 29.8 Mm.

24. A method for determining the growth rate of E. coli host cells that [results in partitioning of a recombinant protein produced by the host cells between the periplasm of the host cells and the supernatant of the culture medium in which the cells are grown that is most suited to the primary recovery of the recombinant protein, wherein expression of the recombinant protein by said cells is under the control of an inducible system, which method comprises:] *facilitates primary recovery of recombinant protein from the periplasm, the method comprising,* a) providing an E. coli host cell culture;

b) changing the growth rate of the E. coli host cells such that the growth rate is in the range of 0.0005 to 0.04/h;

c) inducing expression of the recombinant protein under the control of an inducible system wherein steps (b) and (c) are performed in any order or simultaneously; [and subsequently]

d) determining the yield of recombinant protein in the supernatant of the culture medium and the E. coli host cell periplasm;

e) performing steps (b) and (d), and optionally steps (a) and (c), using a growth rate different from the growth rate initially used in step (b); *and* f) comparing the yield determined in step (d) with the yield determined in step (e); and g) selecting a growth rate from the comparison made in step (f)[, the selected growth rate being in the range of 0.0005 to 0.0092/h, the selected growth rate being most suited to the primary recovery of the recombinant protein from the periplasm];

*wherein the growth rate is in the range of 0.0005 to 0.0092/h.*

25. The method according to claim 24 wherein the yields compared in step (f) are from at least two cultures grown simultaneously.

26. The method according to claim 24 wherein the yields compared in step (f) are from at least two cultures grown sequentially.

27. The method according to claim 24 wherein the yields compared in step (f) are from one culture grown at at least two different growth rates by carrying out steps (a) to (d) using one growth rate in step (b) and then carrying out steps (b) and (d) at least once more varying the growth rate in step (b) each time.

28. The method according to claim 24 wherein the growth rate in step (b) is reduced.

29. The method according to claim 24 wherein changing the growth rate of the E. coli host cells in step (b) comprises adjusting the level of carbon available to the cells.

30. The method according to claim 29 wherein the carbon source is selected from glucose, lactose, sucrose, fructose, glycerol, succinate and lactate.

31. The method according to claim 30 wherein the carbon source is glycerol.

32. The method according to claim 24 wherein changing the growth rate of the E. coli host cells in step (b) comprises adjusting the level of phosphate available to the cells.

33. The method according to claim 24 wherein changing the growth rate of the E. coli host cells in step (b) comprises adjusting the level of oxygen available to the cells.

34. The method according to claim 24 wherein the recombinant protein is targeted to the periplasm.

35. The method according to claim 34 wherein the growth rate selected in step (g) is a growth rate at which greater than 80% of the recombinant protein produced by the host cells is expressed in the periplasm.

36. The method according to claim 24 wherein the recombinant protein is targeted to the supernatant.

37. The method according to claim 36 where wherein the growth rate selected in step (g) is a growth rate at which greater than 80% of the recombinant protein produced by the host cells is produced in the supernatant.

38. The method according to claim 24 wherein the inducible system comprises a lac derived promoter.

39. The method according to claim 38 wherein the lac derived promoter is lac, tac or trc.

40. The method according to claim 38 wherein the promoter is induced with lactose or IPTG.

41. The method according to claim 24 wherein the recombinant protein is an antibody or fragment thereof.

42. The method according to claim 41 wherein the recombinant protein is an antibody that is an IgG.

43. The method according to claim 41 wherein the recombinant protein is an antibody fragment that is a Fab, Fab', $F(ab')_2$ or scFv.

44. A method of producing a recombinant protein in E. coli host cells wherein [expression of the recombinant protein by said cells is under the control of an inducible system and the partitioning of the recombinant protein between the supernatant of the culture medium in which the cells are grown and the periplasm of the host cells is most suited to the primary recovery of the recombinant protein said method] *primary recovery of the protein is from the periplasm, the method,* comprising, a) providing an E. coli host cell culture;

b) changing the growth rate of the E. coli host cells such that the growth rate is in the range of 0.0005 to 0.04/h;

c) inducing expression of the recombinant protein *under the control of an inducible system* wherein steps (b) and (c) are performed in any order or simultaneously; [and subsequently]

d) determining the yield of recombinant protein in the supernatant of the culture medium and the E. coli host cell periplasm;

e) performing steps (b) and (d), and optionally steps (a) and (c), using a growth rate different from the growth rate initially used in step (b);

f) comparing the yield determined in step (d) with the yield determined in step (e);

g) selecting a growth rate in the range of 0.0005 to 0.0092/h from the comparison made in step (f) [the selected growth rate being most suited to the primary recovery of the recombinant protein from the periplasm]; and h) growing the E. coli host cells at the growth rate selected in step (g).

45. The method according to claim 44 wherein the recombinant protein produced is subsequently purified.

46. The method of claim 44 wherein E. coli host cells are grown in a phosphate concentration in the range of 26.9 to 29.8 Mm.

* * * * *